United States Patent [19]
Sakariassen

[11] Patent Number: 5,583,043
[45] Date of Patent: Dec. 10, 1996

[54] COVER SLIP HOLDER FOR BILATERAL AND UNILATERAL SIMULATION OF THROMBOGENESIS IN PARTLY OCCLUDED BLOOD VESSELS AND USE THEREOF

[75] Inventor: Kjell S. Sakariassen, Oslo, Norway

[73] Assignee: Hafslund Nycomed As, Oslo, Norway

[21] Appl. No.: 170,273

[22] PCT Filed: Jun. 29, 1992

[86] PCT No.: PCT/NO92/00117
§ 371 Date: Apr. 18, 1994
§ 102(e) Date: Apr. 18, 1994

[87] PCT Pub. No.: WO93/00989
PCT Pub. Date: Jan. 21, 1993

[30] Foreign Application Priority Data

Jul. 3, 1991 [NO] Norway ................................. 912610
Jun. 5, 1992 [NO] Norway ................................. 922247

[51] Int. Cl.⁶ .................................................. C12M 3/00
[52] U.S. Cl. ................... 435/284.1; 435/286.5; 435/288.3; 435/288.7; 435/808; 422/104
[58] Field of Search .......................... 435/2, 283, 291, 435/808, 284.1, 286.5, 288.3, 288.7; 422/104

[56] References Cited

U.S. PATENT DOCUMENTS 5,278,048 1/1994 Parce et al. .......................... 436/29

FOREIGN PATENT DOCUMENTS 0167706 7/1984 European Pat. Off. ....... G01N 27/28
0242280 4/1986 European Pat. Off. .......... B01F 5/02

OTHER PUBLICATIONS

Sakariassen, Arteriosclerosis, vol. 10, No. 2, 1990.
Hantgan, et al, Blood, vol. 76, No. 21, Jul. 1990.
Sakariassen, J. of Lab. and Clin. Medicine, vol. 102, No. 4, Oct., 1983.
R. M. Barstad, et al., A Perfusion Chamber Developed to Investigate Thrombus Formatin and Shear Profiles in Flowing Native Human Blood at the Apex of Well–Defined Stenoses, *Arteriosclerosis and Thrombosis,* vol. 14, No. 12, Dec. 1994, pp. 1984–1991.

*Primary Examiner*—David A. Redding
*Attorney, Agent, or Firm*—Faegre & Benson

[57] ABSTRACT

The invention relates to a perfusion chamber 1, a mixing device 21, and a cover slip holder 6 for use together with the perfusion chamber 1. The bottom of the cover slip holder 6 is provided with cross-located grooves 11, 12, 13-1 for installing cover slips 14, 15, 16-1, and in which the cover slips 14, 15, 16-1 are positioned in comparison to each other in such a way that the cross-sectional area of the flow channel 4 is constricted unilaterally, for simulation of thrombogenesis in human blood vessels with stenosis. The bottom of the perfusion chamber 1, in the measure chamber 7, can also have an elevation into the flow channel 4 in the measure chamber 7 which together with the recessed cover slip holder bottom produces a bilateral constriction of the cross-sectional area of the measure chamber 7. A mixing device 21 is connected to the system upstream of the perfusion chamber 1 and produces homogeneous mixing of solutions added to the blood flow. The use of the perfusion chamber 1, the cover slip holder 6 and the mixing device 21 is described.

16 Claims, 4 Drawing Sheets

U.S. Patent Dec. 10, 1996 Sheet 1 of 4 5,583,043
Fig. 1
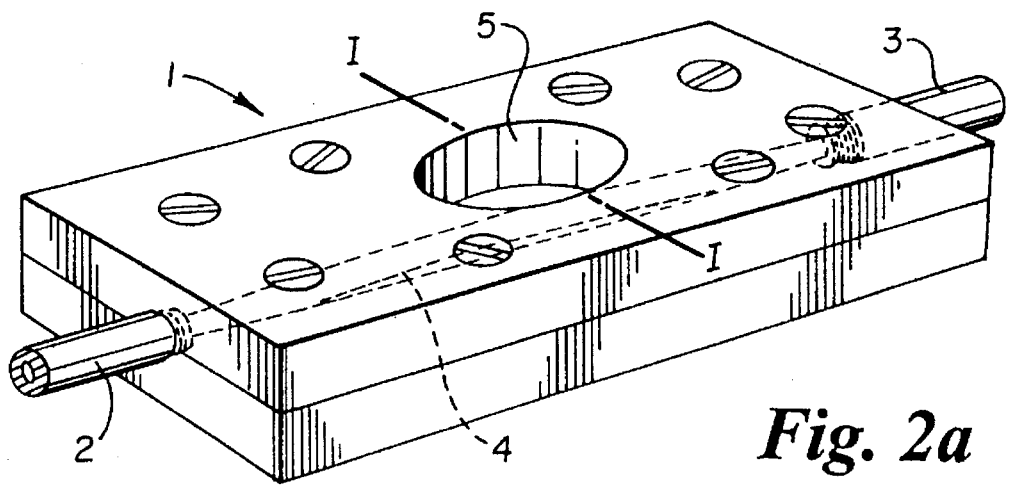
Fig. 2
Fig. 2a
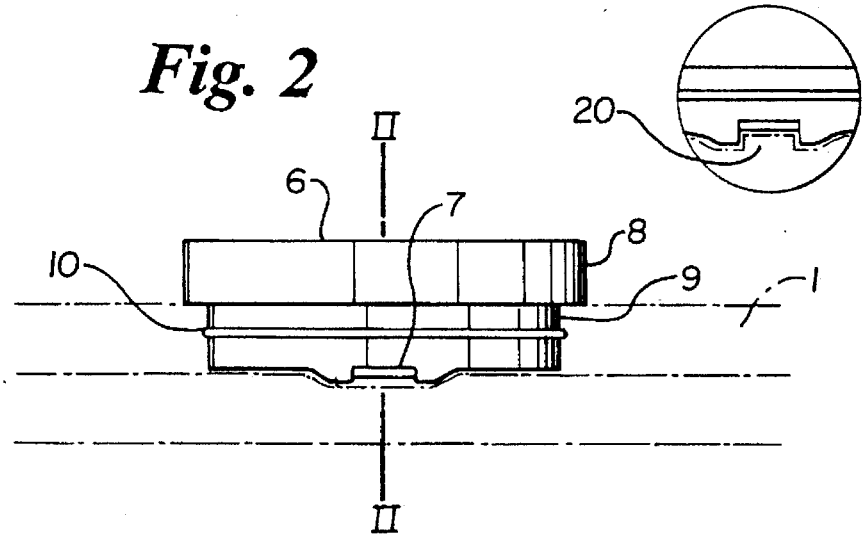
Fig. 3
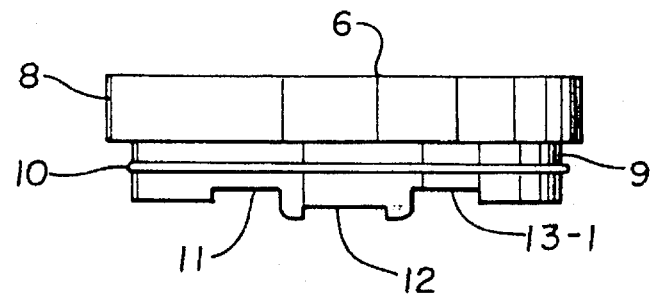

COVER SLIP HOLDER FOR BILATERAL AND UNILATERAL SIMULATION OF THROMBOGENESIS IN PARTLY OCCLUDED BLOOD VESSELS AND USE THEREOF

The invention relates to a cover slip holder as described in the preamble of claim 1, for simulation of in vivo blood flow conditions in occluded blood vessels. The invention also relates to the accompanying parallel-plate perfusion chamber including the cover slip holder. One preferred embodiment of the perfusion chamber is when it is connected to a mixing device for mixing in vitro added solutions to the blood flow before reaching the parallel-plate perfusion chamber.

The cover slip holder according to the present invention is inserted in a parallel-plate perfusion chamber, so that the bottom of the knob creates the roof/floor of a measure chamber and in the bottom of the knob a varying number of glass slides or cover slips, made of plastic or glass or any other material, are attached in specially made grooves. These cover slips can/cannot be covered with a biological/synthetic material, and the surface levels of the cover slips vary in relation to each other and to the roof/floor of the measure chamber, to produce a varying unilateral constriction of the cross-sectional area of the flow slit. Bilateral constriction of the flow cross-sectional area can, in a special embodiment, be obtained by elevating an area of the bottom of the measure chamber, facing the cover slips of the cover slip holder. Minimum 20 mm upstream of the blood flow inlet of the parallel-plate perfusion chamber, preferably a mixing device functioning according to the venturi-principle, can be installed in the flow channel. A device in which blood is exposed to materials facilitating thrombogenesis under conditions simulating blood flow in human blood vessels is beneficial both for research and industry in the medical field. By puncturing a human vein, inserting a venous catheter which is connected, by plastic tubes, with a parallel-plate perfusion chamber, and a pump, located downstream to the parallel-plate perfusion chamber, it is possible to maintain ex vivo (i.e. anti-coagulation is not used) blood flow through a perfusion chamber. In this connection, an annular perfusion chamber has previously been constructed, in which flowing blood was brought in close contact with human subendothelium, digested with αa-chymotrypsin which produced a surface which was rich in collagenous fibrils (Baumgartner, H. R., Microvasc. Res. 5: 167, 1973). Collagenous fibrils are shown to be active in promoting aggregation of platelets in flowing blood (Baumgartner, H. R., Thromb. Haemost. 37: 1, 1977). More recently, perfusion chambers with rectangular cross-section of the blood flow slit have been constructed, in which a commercially available glass slide or plastic cover slip is attached in a specially made groove, located 90° on the flow direction. This glass slide or plastic cover slip, which surface is on the same level as that of the roof of the chamber, was covered by biological material (endothelial cells, connective tissue from endothelial cells and collagen) to promote thrombogenesis (Sakariassen, K. S., Aarts, P. A.M. M., de Groot, P. G., Houdijk, W. P.M., Sixma, J. J. J. Lab. Clin. Med. 102: 522, 1983). This perfusion chamber has a flow channel, in which the cross-section is changed from circular in the supply tubing to rectangular in the measure chamber and back to circular, usually accompanied by changed cross-sectional area. Such changes can lead to labile flow conditions or flow separation in the measure chamber. The perfusion chamber was therefore modified such that the transition from circular to rectangular dimensions of the flow channel was smooth. It was calculated that the reduction of the pressure gradient in this system, owing to the lesser kinetic energy, was less than 5% of the acting viscous force. This indicates laminar flow condition in the perfusion chamber (Sakariassen, K. S., Joss, R., Muggli, R., Kuhn, H., Tschopp, T. B., Sage, H., Baumgartner, H. R., Arteriosclerosis, 10: 276–284, 1990).

The mentioned modified perfusion chamber makes possible an ex vivo test system for simulation of in vivo blood flow conditions by utilizing non-anticoagulated blood. Activation of platelets and coagulation proximal to the perfusion chamber is minimal and within normal range. The perfusion chamber has a well defined thrombogenic surface which triggers thrombus formation. Accordingly, the system is very well suited for testing effects of medicaments and compositions facilitating/inhibiting thrombogenetic processes.

However, the mentioned perfusion chamber offers no possibility of testing the mentioned compositions under blood flow conditions simulating partly occluded blood vessels, which in vivo occur in atheromatosis and atheroschlerotic blood vessels, and which is an important cause for thrombogenesis. Similarly, adding solutions to a blood flow tube before the perfusion chamber will very often give incomplete mixing due to the laminar flow conditions. However, simulation of blood flow conditions in partly occluded blood vessels can be obtained in the present invention, by profilating the bottom of the cover slip holder with at least two different levels, such that local variation in the cross-sectional area in the measure chamber occurs. Cover slips, with the surfaces coated with biological/synthetic material, can be attached to the bottom of the cover slip holder, which produces the constriction of the flow channel, and in addition immediately proximal and distal to the constriction. Hence, it will be possible to examine thrombus formation proximal, on and distal to the constriction on cover slips without coated surfaces, surfaces coated with biological materials activating coagulation (procoagulant surfaces), or coated with biological material not activating coagulation (non-procoagulant surfaces), or covered with native polymeric chemical compositions, in addition to the action of medicaments.

Normal in vivo blood circulation is characterized by laminar blood flow conditions. Thrombotic processes are frequently encountered at areas of constricted vessels. Such conditions disturb the laminar blood flow. The flow channel in the present perfusion chamber has a smooth and gradual transition from circular to rectangular dimensions of the flow slit, the purpose of which is to maintain laminar blood flow conditions all the way to the central measure chamber. This is important, since disturbed blood flow may activate platelets and coagulation factors proximal to the central measure chamber. In the central measure chamber, which is created when the cover slip holder is inserted in the well in the perfusion chamber, the roof and/or bottom is profilated, to constrict the flow cross-sectional area, which disturbs the laminar blood flow. Thus, a situation of an in vivo stenosis is simulated. In addition the cover slips proximal, on and distal to the constriction can be coated, or not coated, with a material which activates, or does not activate, coagulation, thus simulating in vivo vessel wall lesions.

In order to examine the effect of for example experimental anti-thrombotics on the thrombogenesis, which are added to the blood stream proximally to the perfusion chamber, preferably a mixing device is installed. This device secures homogenous mixing of the material added to the blood flow before it enters the perfusion chamber. To ensure that the flow of blood is laminar at the entrance of the perfusion chamber, the mixing device should be installed at a distance of at least 20 mm upstream to the perfusion chamber. The mixing device comprises a T-tube, in which the cross tube provides the main blood flow channel, and the addition of materials is performed through the side tube. The diameter of the flow channel is then constricted gradually and then suddenly expanded. This shape of the flow channel creates turbulent flow conditions which facilitate mixing of solutions added to the blood stream through the side tube, upstream to the constriction, and secures homogenous mixing of the added material in the blood.

The parallel-plate perfusion chamber with the cover slip holder and possibly in connection with the mixing device are according to the invention characterized by the features as indicated in the claims.

Ex vivo-testing also means that normal venous and arterial flow conditions can be simulated. It is demonstrated that the wall shear rate close to the wall or to the cover slip in the perfusion chamber is important for the deposition of platelets and for activation of coagulation (Sakariassen, K. S., Joss, R., Muggli, R., Kuhn, H., Tschopp, T. B., Sage, H., Baumgartner, H. R., Arteriosclerosis, 10: 276–284, 1990, Sakariassen, K. S., Weiss, H., Baumgartner, H. R., Thromb. Haemostas, 65:596–600, 1991. The wall shear rate in flow channels with rectangular flow cross-section can be expressed by formula I $$\gamma_{wall} = 1,03 \frac{6Q}{a \cdot b^2} \qquad I$$

in which $\gamma_{wall}$ represents the wall shear rate (sec$^{-1}$)

Q represents the blood flow in ml/s, a represents the width (cm) of the rectangular flow channel, and represents the height (cm) of the rectangular flow channel.

By varying these dimensions of the flow channel, venous and arterial shear rates respectively, can be simulated in the perfusion chamber.

Development of a stenosis in vivo can have an eccentric progress when it is developed from atheromatic conditions in the vessel wall. Simulation of such conditions can be obtained according to the present invention by an eccentric constriction of the flow channel by profilating, the bottom of the cover slip holder in the direction of the blood flow.

The figures show a preferred embodiment of the cover slip holder according to the invention, with three cover slips and the location of the cever slip holder in the perfusion chamber.

BRIEF DESCRIPTION OF THE DRAWINGS

FIG. 1 shows the perfusion chamber 1 with a flow inlet connector 2 of standard type for connection to an arm vein via an infusion kit. A corresponding flow outlet connector 3 for connecting the perfusion chamber to a pump device. The flow channel 4 connects the inlet connector with the outlet connector and passes through a bored, elliptic well 5, in which the cover slip holder 6 according to the invention is inserted.

FIG. 2 shows the cover slip holder 6 according to the invention in a section 90° (or perpendicular) to the flow direction (along the line I—I in FIG. 1), in which the bottom creates the roof of the measure chamber 7 when the cover slip holder is inserted in the perfusion chamber, and an O-ring 10 for sealing purposes. Insertion of the cover slip holder 6 in the perfusion chamber 1 (dotted draft) is shown.

FIG. 2A shows a detail of a special embodiment of the invention, in which bilateral constriction of the flow channel is obtained by elevating the bottom of the measure chamber 20, facing the cover slips on the bottom of the cover slip holder.

FIG. 3 shows the cover slip holder 6 according to the invention in a section along the flow channel (along the line II—II in FIG. 2) with grooves 11, 12, 13-1 adapted to commercially available plastic cover slips.

DETAILED DESCRIPTION OF THE INVENTION

Figure 3A:
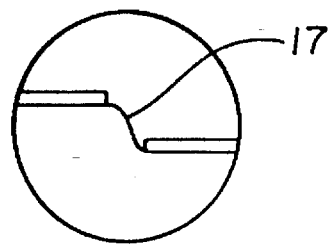
FIG. 3A–3C show three examples of the sinusoidal wall of the elevation of the cover slip holder creating the constriction of the flow cross-sectional area in the measuring chamber.

The cover slip holder 6 according to the invention is inserted in well 5 into the perfusion chamber 1 at a distance from the perfusion chamber inlet which is necessary to establish laminar blood flow conditions proximal to cover slip 14, positioned upstream to the constriction of the flow channel. This distance is at least 50 mm, preferably 70 mm. The parallel-plate perfusion chamber is constructed from a solid plastic material (for example polymethyl acrylate) and comprises two plates, placed adjacent to each other and secured by screws, as shown in FIG. 1. The elliptic well 5 is made as a hole in the upper plate. In the lower plate a groove is constructed, which, when the plates are placed adjacent to each other, creates the flow channel 4. The measure chamber 7 is defined as that part of the flow channel which is limited by the walls of the elliptic well 5. At the place of the elevation of the bottom of the cover slip holder 6, creating the constriction of the flow channel, the bottom of the cover slip holder 6 is formed as a cross-located (compared to the flow direction), curved elevation which is fitted to a correspondingly curved depression, cut into the lower plate of the parallel-plate perfusion chamber. The dimensions of the flow channel (a, b) are selected by using formula I, in accordance with the shear rates and flow conditions which are necessary to obtain the wanted simulated conditions.

The cover slip holder 6 is produced of the same material as the parallel-plate perfusion chamber and consists of a body, for example formed as a cylinder with an elliptic cross-section 9 corresponding to the well 5 in the perfusion chamber (FIG. 2). In the upper part of the cylinder a handle 8 can be made by increasing the cross-section of the body, with the same form as the elliptic cylinder 9, located such that the height of the cylinder 9 is equal to the thickness of the upper plate in the parallel-plate perfusion chamber. An O-ring 10 of suitable dimension is located around the cylinder 9 in order to prevent possible leakage of blood from the measure chamber.

Figure 3B:
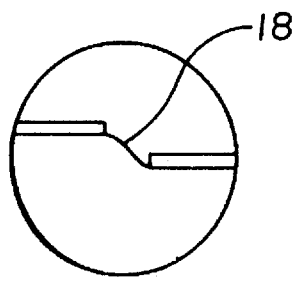
Figure 3C:
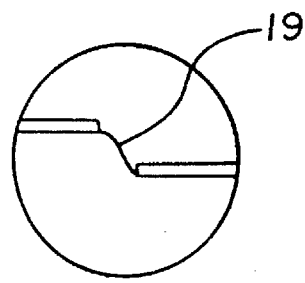
Figure 4:
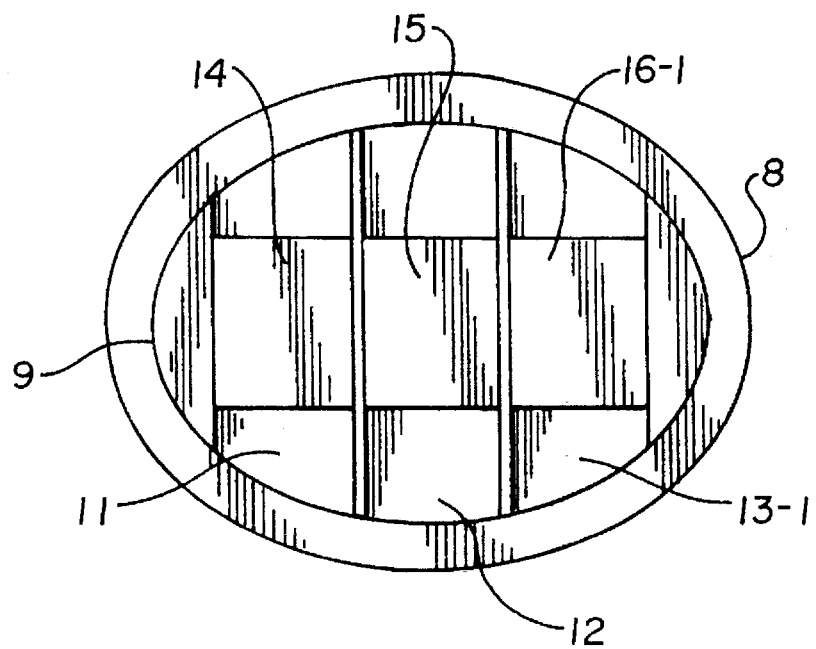
FIG. 4 shows the cover slip holder 6 according to the invention seen from above, with three cover slips 14, 15, 16-1 placed in the grooves 11, 12, 13-1 in the bottom of the cover slip holder.

Partly eccentric occlusion of a blood vessel is simulated by profilating the bottom of the cover slip holder 6 in the flow direction. Cover slip grooves 11, 12, 13-1 are produced in the bottom of the cover slip holder, 90° on the flow direction. The debth of these grooves 11, 12, 13-1 equals the thickness of the cover slips and the distance between the grooves is 0,5 mm. The cover slips are attached in the grooves with a suitable attachment means. The cover slip grooves can also be permanently filled with a mass of any kind of material with the same thickness as the cover slips, in which case thrombus formation is initiated on a base which cannot be removed from the cover slip holder for examination. The proximal cover slip 14 in the roof of the measure chamber is on a level with the roof of the flow channel 4 in the perfusion chamber 1. The fundament of the groove 12 of the second cover slip 15 downstream is elevated, with straight or curved (for instance sinusoid) walls 17, 18, 19, in relation to the roof of the flow channel 4, in such a way that the cross-sectional area of the measure chamber is constricted in relation to the cross-sectional area of the flow channel. The level difference between the proximal (14) and middle (15) cover slip can vary in such a way that the cross-sectional area of the measure chamber at this place can be occluded up to 95% of the cross-sectional area of the flow channel 4. The grooves for the distal cover slips 16-1 to 16-4 (only 16-1 is shown in FIG. 3) can for instance be levelled with the proximal cover slip groove 11 or the level can be changed in relation to the first cover slip groove 11. The size of the cover slip holder 6 is adjusted according to the desired number of cover slips, which at least is 1 and is preferably between 1 and 6.

Partial concentric occlusion of a blood vessel is simulated by elevation of the bottom 20 of the measure chamber 7 in the perfusion chamber 1 into the measure chamber 7, in such a way that the cross-sectional area of the flow channel is constricted bilaterally, both from the roof and bottom of the measure chamber.

The surface of the cover slips can be uncoated or coated with biological material, or chemical compositions which it is desirable to test. Biological materials, which may be mentioned, are living cells, previously stimulated or non-stimulated. Non-procoagulant material may comprise collagenous fibrils, non-stimulated cultures of human endothelial cells and extracellular connective tissue deposited from the mentioned endothelial cells or components thereof. Procoagulant material may comprise human endothelial cells treated with, for instance, endotoxine or cytokines, and connective tissue deposited by the treated endothelial cells or components thereof. In addition, the biological material may comprise compounds produced by recombinant DNA technology. Synthetic chemical compositions which modify, or do not modify, thrombotic processes will also represent possible coats or films on the exposed surfaces of the cover slips. Thus all coats of biological material, recombinant material and synthetic compounds (medicaments), with our without effect on thrombotic processes are regarded to be within the idea and scope of the invention. The procedures for coating the cover slips are known from the literature.

A typical perfusion experiment lasts for instance 5 min and requires 50 ml blood (10 ml/min) from the blood donor. The blood perfusion is directly followed by a 20 s perfusion (10 ml/min) with a physiological buffer solution which washes out the blood from the perfusion chamber, and then followed by a 40 s perfusion (10 ml/min) with a solution which fixes the thrombotic deposits on the reactive surface in the perfusion chamber. The reactive surface with the fixed thrombotic material is subsequently removed from the perfusion chamber and embedded in plastic (Epon). 1μm thin sections are produced from the cast material, stained and morphologically evaluated by the use of light-microscopy and an image analyzing system. The size of the thrombus on the reactive surface is expressed as volume of the thrombus per surface unit.

Figure 5:
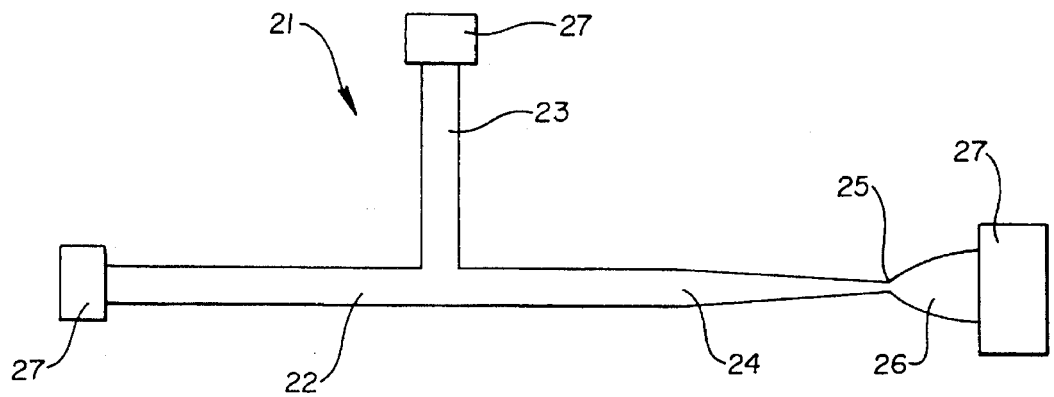
FIG. 5 shows a mixing device 21 for homogenous mixing of solutions added to the blood flow.

When the perfusion chamber 1 with the cover slip holder 6 is used for examining the effect of substances added to the blood in vitro, the mixing device 21 is used, installed into the flow channel between the vein and the perfusion chamber 1. The mixing device 21 comprises a modified T-tube, as shown in FIG. 5, in which the side tube 23, equipped with a standard connector 27, allows pumping or injection of optional solutions into the blood flowing through the main tube 22, which is equipped with standard connectors 27 in both ends. The inner diameter of the main tube or blood flow tube 22 and side tube 23 can preferably be 2,0 mm, or be adapted to the existing experimental conditions. At a suitable distance downstream of the side tube 23, for example 12 mm, the blood flow tube is gradually constricted over a suitable distance 24, for example 12 mm, to a point 25 with for example inner diameter of 0,5 mm, thereafter the tube is expanded over a considerably shorter distance 26, for examples 5 mm, to a diameter considerably larger than the diameter of the blood flow tube 22, for example 4,0 mm. By adding a solution through the side tube 23 the blood flow will remain laminar until the smallest diameter of the tube 25 and the mixing of the added solutions will be inadequate, whereafter the sudden increase of the diameter over the short stretch of tube 26 creates turbulent flow conditions, providing homogenous mixing of the solutions added to the blood flow.

In a preferred embodiment, in contrast to the mentioned gradual expansion over a considerably shorter distance 26, describing a curved pattern (FIG. 5) this expansion is immediate and the tube reaches its new diameter in a pattern perpendicular to the flow direction, giving optimal mixing flow conditions.

In order to secure that laminar flow conditions are reinstated before the blood flows into the perfusion chamber 1, the mixing device 21 is located at least 20 mm upstream of the inlet connector 2 in the perfusion chamber 1.

The following examples illustrate the present invention.

EXAMPLE 1

Non-anticoagulated human blood was drawn directly from an anticubital vein over three cover slips. Purified human collagen, was coated on cover slip 15 and endothelial cells on cover slips 14 and 16-1 on the cover slip holder 6 in the measure chamber 7. The anticubital vein was punctured by a "butterfly" infusion needle and the blood was drawn through the blood flow channel 4 to the measure chamber 7 by a pump, placed distally to the perfusion chamber. The blood flow was 10 ml/min and the perfusion lasted from 1 to 15 min. The thrombi on the cover slip with collagen at the constriction of the flow channel in the measure chamber partly occluded the blood flow through the chamber after 3 min, when the occlusion initially constricted the blood flow channel with >80%. Occlusion of the blood flow channel <60% produced smaller thrombi. All the occluded chambers produced significant thrombogenesis within 1 min.

The perfusion chamber was perfused for 20 s with a physiological buffer solution immediately after the blood perfusion, followed by a perfusion for 40 sec with a glutaraldehyde solution to fix the thrombus. All perfusions were performed with continous flow through the chamber, by means of T-tubes, without stopping the pump.

EXAMPLE 2

This example relates to a comparison of thrombogenesis in a measure chamber without profiled bottom of the cover slip holder with that of a measure chamber according to the invention, in which the bottom of the cover slip holder is elevated to simulate arterial stenosis with shear rates equal to 2600 $s^{-1}$.

Non-anticoagulated blood from an anticubital vein was pumped through the perfusion chamber with the cover slip holder according to the invention, with a flow rate of 10 ml/min, as described in Example 1. The elevation of the bottom in the cover slip holder occluded 50% of the cross-sectional area of the flow channel and created an unilateral stenosis. A cover slip on the constriction was coated with purified human collagen. The shear rate at the surface of this cover slip was 2600 $s^{-1}$. This equals a shear rate which can be observed in a coronary artery of average size with a 50% occluding stenosis. The measure chamber without a cover slip holder with elevated bottom was dimensioned so as to create shear rates of 2600 $s^{-1}$ in the measure chamber.

Figure 6:
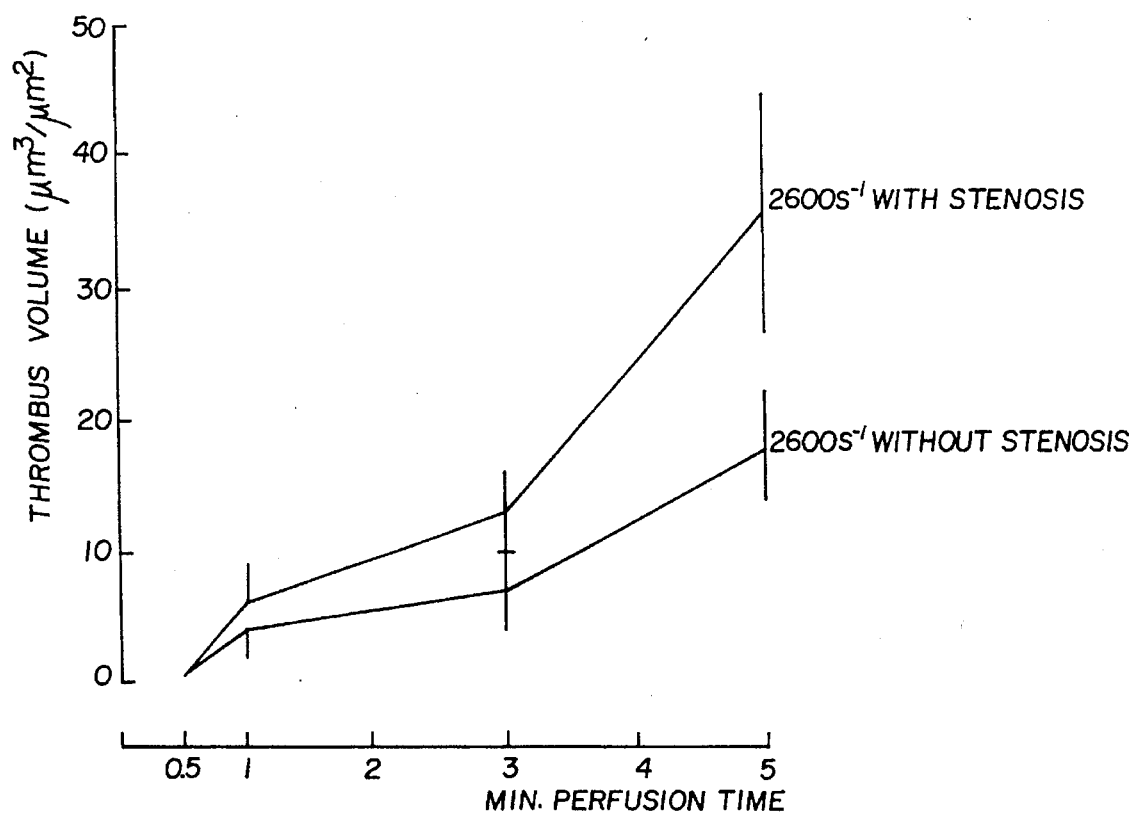
FIG. 6 shows thrombus volume ($\mu m^3/\mu m^2$), as a function of perfusion time, in a measure chamber without elevation into the flow channel of the bottom of the cover slip holder (without stenosis) and in a measure chamber according to the invention with profilated bottom of the cover slip holder (with stenosis). The volumes of the thrombi are given as mean values ± S.E.M. and n =5–7.

As shown in FIG. 6 the volume of the thrombus, measured with an image analysis technique, was already after 3 min's perfusion significantly larger in the occluded measure chamber according to the invention and doubled after 5 min, compared to the thrombus volume in the measure chamber without occlusion. This demonstrates the impact of an initial occlusion in the measure chamber in order to simulate the development of thrombogenesis in vivo vessel systems with stenosis.

EXAMPLE 3

Testing the efficiency of the mixing device

The test equipment comprised the mixing device 21 (FIG. 5) connected to a 20 mm tubing of the same dimension, which was connected to four equally long, parallel tubes with equal flow cross-sectional areas (¼ of the flow cross-sectional area of the main flow). This assembly caused a blood flow through the mixing device to separate into four equivalent flows. Citrated blood was pumped through the mixing device (10 ml/min) as described in Example 1, while a solution of physiological saline containing $^{51}CrO_4$ was continuously added (0,1–1 ml/min) through the side-tube 23. The four sub-flows were collected and the radioactivity measured.

In order to examine the mixing efficiency without the mixing device, this was replaced by a T-tube without constriction and the following expansion, but with the same dimensions and length as the mixing device.

Figure 7:
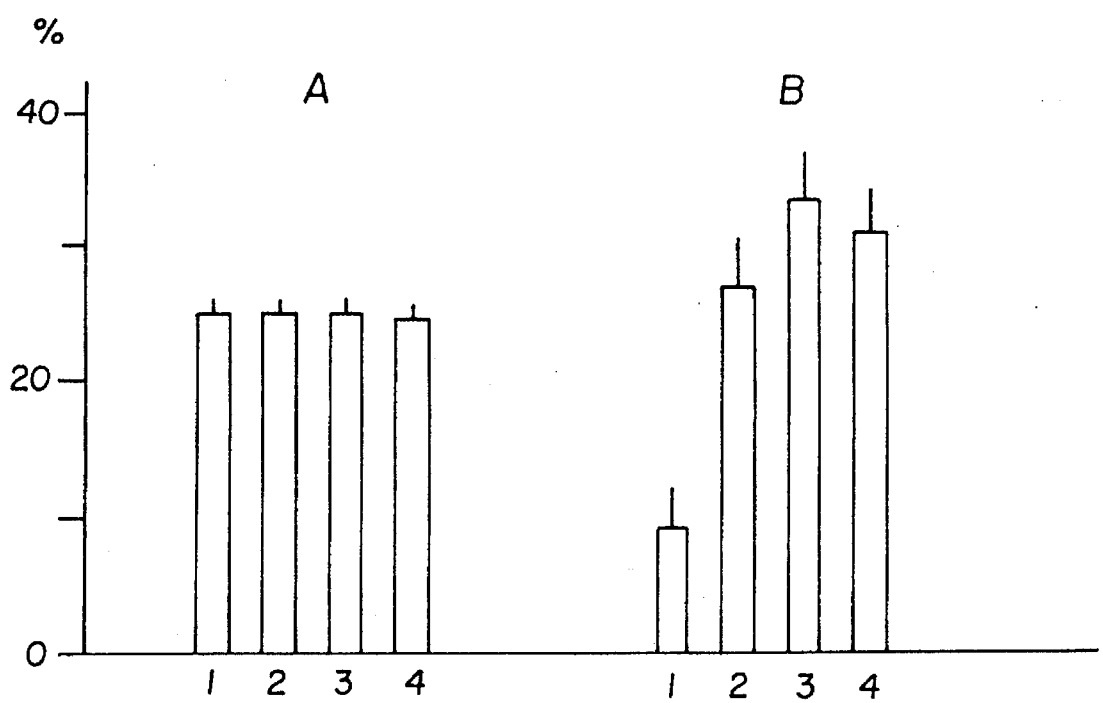
FIG. 7 shows the percentage distribution of radioactivity in four parallel, equal sub-flows of the main flow (10 ml/min) of citrated blood after injecting or pumping (0,1–1 ml/min) a solution, containing $^{51}CRO_4$ in physiological saline, through the side tube 23 in the mixing device (panel A). The sampled, equal sub-flows are connected downstream of the mixing device. Panel B shows a similar test without using the mixing device according to the invention. The results are expressed as mean values ± S.D., $n_A=6$ (with the mixing device), $n_B=3$ (without the mixing device).

FIG. 7 shows no significant difference in the percentage radioactivity (% of the injected radioactivity in the side tube) in the four sub-flows, in the test in which the mixing device 21 was used (A). When a solution of physiological saline, containing $^{51}CRO_4$, was injected in the main flow, and this flow was not led through the mixing device, considerable differences in percent radioactivity collected from the four sub-flows appeared (B). This demonstrates that the mixing device produces a homogenous mixing of the radioactivity in the blood stream. This did not happen in the absence of the mixing device.

I claim:

1. A cover slip holder for insertion in a perfusion chamber which comprises two plates, with a through-running flow channel having a smooth, gradual transition from circular cross-section to rectangular cross-section, wherein:

the cover slip holder comprises a body, with means for sealing to a hole of equal cross-section in the perfusion chamber, and a bottom of the cover slip holder has cross-running grooves oriented at a 90° angle to a direction of flow through the flow channel, the grooves for attaching removable cover slips, the depth of the grooves is equal to a thickness of the cover slips, and the bottom of the cover slip holder is profiled in the direction of flow in such way that, when the cover slip holder is placed in the perfusion chamber, a lower surface of a first cover slip is level with a roof of the flow channel, a lower surface of a second cover slip is recessed down into the flow channel in a measure chamber in comparison to the lower surface of the first cover slip, forming straight of sinusoidal side walls, and the measure chamber is defined between the lower surfaces of the cover slips and a bottom of the perfusion chamber therebeneath, so that a cross-sectional area of the measure chamber is constricted unilaterally, or constricted bilaterally with an elevation in a bottom of the measure chamber elevated toward the lower surfaces of the cover slips, and so that a lower surface of any cover slip following after the second cover slip on the bottom of the cover slip holder, is independently either level with the lower surface of the first cover slip or is recessed down into the flow channel in the measure chamber in comparison to the lower surface of the first cover slip.

2. A cover slip holder according to claim 1, wherein the cover slip holder is a cylinder with elliptic cross-section.

3. A cover slip holder according to claim 1, wherein the lower surface of the second cover slip is recessed down into the measure chamber compared to the lower surface of the first cover slip, occluding the cross-sectional area of the measure chamber unilaterally from more than 0% to 95% of the cross-sectional area of the flow channel.

4. A cover slip holder according to claim 1, wherein the walls are sinusoidal walls 90° to the flow direction.

5. A cover slip holder according to claim 1, wherein the number of cover slips is upwardly limited by the shape of the cover slip holder.

6. A cover slip holder according to claim 1, wherein at least one of the lower surfaces of the cover slips is coated with a biological, recombinant, or synthetic chemical material, or a combination thereof, optionally influencing thrombogenesis.

7. A cover slip holder according to claim 1, wherein the cover slip holder is produced of hard plastic or hard transparent plastic.

8. A cover slip holder according to claim 1, wherein the cover slips are replaced by a permanent, non-removable material, with the same thickness as the cover slips.

9. In combination with the cover slip holder of claim 1, a perfusion chamber which comprises two plates, with a through-running flow channel having a smooth, gradual transition from circular cross-section to rectangular cross-section, and further comprising an elevation, having sinusoidal walls 90° to the flow channel direction, in the bottom of the measure chamber, toward the recessed lower surface of a cover slip, so that the cross-sectional area of the measure chamber is constricted bilaterally more than 0% and less than 95% of the cross-sectional area of the flow channel.

10. The combination of a cover slip holder and a perfusion chamber according to claim 9, wherein the bottom of the measure chamber is level with the bottom of the flow channel and the cross-sectional area of the measure chamber is constricted unilaterally more than 0% and less than 95% of the cross-sectional area of the flow channel.

11. The combination of a cover slip holder and a perfusion chamber according to claim 9, having a mixing device comprising a side tube equipped main tube, in which a diameter of the main tube gradually diminishes to a considerably smaller value followed by an immediate increase to a diameter considerably larger than the main tube diameter, and including a cover slip holder according to claim 1.

12. A cover slip holder according to claim 1, wherein the cover slips are plastic or other synthetic material, such as glass.

13. A cover slip holder according to claim 1, wherein the means for sealing is an O-ring.

14. A cover slip holder according to claim 1, wherein the number of cover slips is up to 6.

15. A cover slip holder for insertion in a perfusion chamber which comprises two plates, with a through-running flow channel having a smooth, gradual transition from circular cross-section to rectangular cross-section wherein:

the cover slip holder comprises a body, with means for sealing a hole of equal cross-section in the perfusion chamber, and a bottom of the cover slip holder has at least one cross-running groove 90° to a direction of flow for attaching at least one removable cover slip, the depth of the groove is equal to a thickness of the cover slip, and the bottom of the cover slip holder is profiled in the direction of flow in such way that, when the cover slip holder is placed in the perfusion chamber, a lower surface of the cover slip is recessed in comparison to the bottom of the cover slip holder, forming straight or sinusoidal side walls, and a measure chamber is defined between the lower surface of the cover slip and a bottom of the perfusion chamber therebeneath, so that a cross-sectional area of the measure chamber is constricted unilaterally, or constricted bilaterally by an elevation in a bottom of the measure chamber elevated toward the lower surface of the cover slip, and adapted so that a lower surface of any cover slip following after the first cover slip on the bottom of the cover slip holder, is independently either level with the lower surface of the first cover slip or recessed in comparison to the lower surface of the first cover.

16. The combination of a perfusion chamber and the cover slip holder according to claim 15, wherein an elevation in the bottom of the measure chamber, elevated toward the lower surface of the cover slip in relation to the measure chamber roof, is elevated into the measure chamber to such a degree that the cross-sectional area of the measure chamber is constricted bilaterally more than 0% and less than 95% of the cross-sectional area of the flow channel.

* * * * *